United States Patent [19]

Faunce

[11] 4,433,959
[45] Feb. 28, 1984

[54] COMPOSITE LAMINATE DENTAL VENEER CONTAINING COLOR SYSTEMS

[75] Inventor: Frank R. Faunce, Jackson, Miss.

[73] Assignee: JAFF Investment Company, Muncie, Ind.

[21] Appl. No.: 361,257

[22] Filed: Mar. 24, 1982

[51] Int. Cl.³ ............................................. A61K 6/08
[52] U.S. Cl. .................................... 433/201; 106/35; 433/199; 433/222; 523/115
[58] Field of Search .................. 106/35; 433/201, 212, 433/222, 223, 202, 199; 523/115

[56] References Cited

U.S. PATENT DOCUMENTS

| | | | |
|---|---|---|---|
| 3,004,343 | 10/1961 | Rydin | 32/13 |
| 3,046,657 | 7/1962 | Menter et al. | 32/12 |
| 3,375,582 | 4/1968 | Myerson | 32/12 |
| 3,423,829 | 1/1969 | Halpern et al. | 32/8 |
| 3,423,831 | 1/1969 | Semmelman | 433/212 |
| 3,483,618 | 12/1969 | Andrew | 32/12 |
| 3,488,846 | 1/1970 | Cornell | 433/212 |
| 3,647,498 | 3/1972 | Dougherty | 32/12 |
| 3,760,502 | 9/1973 | Hirsch | 32/8 |
| 3,986,261 | 10/1976 | Faunce | 32/12 |
| 4,104,798 | 8/1978 | Takahashi et al. | 433/222 |

Primary Examiner—Lorenzo B. Hayes
Attorney, Agent, or Firm—James L. Jackson

[57] ABSTRACT

A composite laminate dental veneer is provided for attachment to the labial enamel surface of a human tooth. In one form of the invention the dental veneer comprises an outer lamination composed of stain-resistant, chemical-resistant and erosion-resistant material and an inner lamination composed of a material having the capability of efficient bonding to the labial enamel surface of the tooth and having the capability of permanent attachment to the outer lamination in such manner as to define an integral veneer mass. The outer lamination may be composed of dense, stain-resistant materials such as cross-linked polymer and various vitreous materials such as ceramic material, glass and the like. The inner lamination may be composed of a noncross-linked polymer or a porous and cellular ceramic, glass or vitreous substance. The laminate veneer also employs a color system embodying an additive color system which includes color pigments of an enamel blend and a subtractive color system which includes color pigments of a dentin color blend. These color pigments would be distributed in color centers or microdots of color that are layered within an matrix.

16 Claims, 7 Drawing Figures

U.S. Patent      Feb. 28, 1984      4,433,959
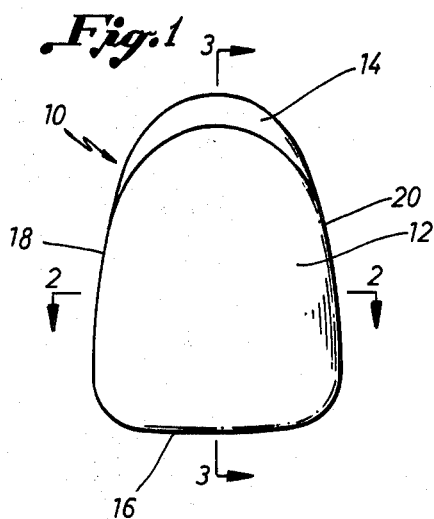
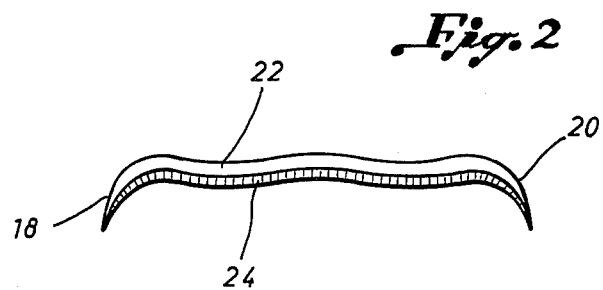
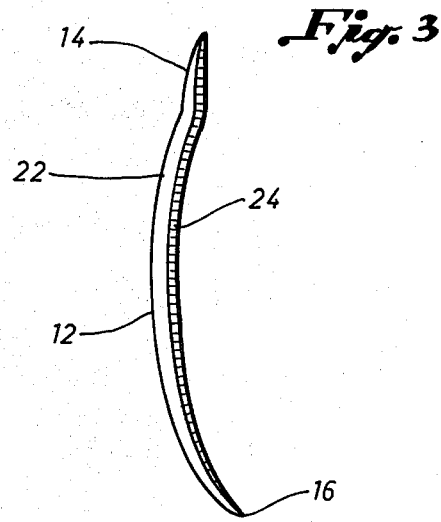
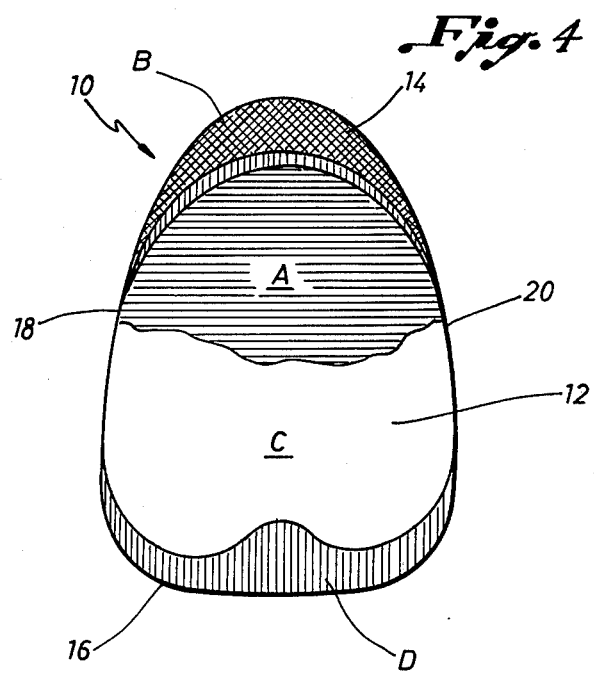
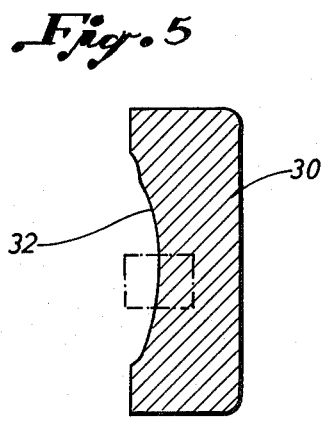
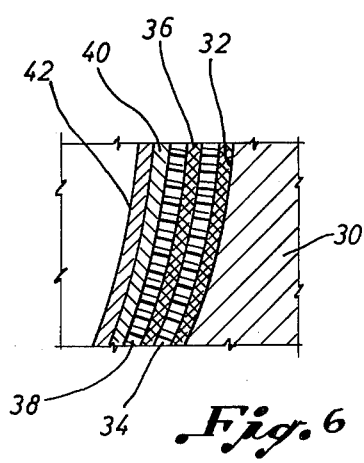
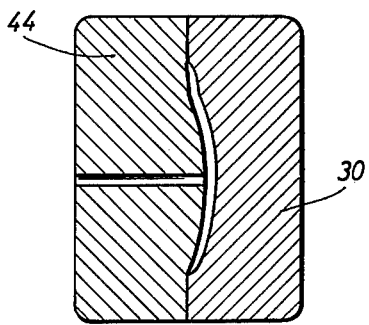

COMPOSITE LAMINATE DENTAL VENEER CONTAINING COLOR SYSTEMS

FIELD OF THE INVENTION

This invention relates generally to dental veneers for attachment to the labial enamel surfaces of a human tooth and more specifically concerns the provision of composite laminate dental veneers which are resistant to stains, chemicals and erosion and which are provided with a color system that renders the appearance thereof substantially identical to that of a natural tooth in light rays of visible wavelength.

BACKGROUND OF THE INVENTION

This invention is related to the invention disclosed in U.S. Pat. No. 3,986,261 of Frank R. Faunce, and constitutes an improvement over the teachings thereof. Dental veneers have been manufactured and sold in accordance with the teachings of the above noted patent. These laminate veneers have been manufactured by molding a single mass of polymer resin suitable for bonding to the enamel surfaces of the patient's teeth. These laminate veneers have also been provided with a uniform color system dispersed throughout the thickness of the laminate veneer. It has been determined that dense polymer materials do not ordinarily have the capability of efficient bonding to a patient's teeth. On the other hand, a relatively porous polymer material such as noncross-linked polymethylmethacrylate has been found quite efficient from the standpoint of bonding the same to the enamel surface of a patient's teeth. This material would bond well with the surfaces of the patient's teeth and thus remain in place for extended periods of time. It has also been determined through patient reports and laboratory analysis that relatively porous polymer compositions have a tendency to become stained after a period of time and are not as resistant to abrasion as is desired for long lasting service. It is therefore desirable to provide a laminate dental veneer having the capability of efficient attachment to the enamel surfaces of the patient's teeth and which is also stain-resistant, chemical-resistant and resistant to erosion.

When noncross-linked polymer materials are employed for the manufacture of laminate dental veneers, the uniform color system thereof, though developing a generally pleasing appearance, does not develop natural characteristics of dental color and appearance. A natural tooth has a degree of translucency and certain intrinsic colors thereof reflect light and provide three-dimensional color characteristics. Color pigments are present in the enamel structure of a human tooth and the enamel is somewhat translucent. Light entering the translucent enamel is reflected, thus reflecting the enamel tooth color. Light waves penetrating the enamel also reflect the color characteristics of the dentin situated below the layer of translucent enamel. On visualizing a tooth therefore the intrinsic colors of the enamel and dentin are present and assist in providing the tooth with a three-dimensional physical appearance and color characteristics. Ideally, a laminate veneer should also have the capability of providing the tooth with a three-dimensional physical characteristic as well as a three-dimensional color characteristic involving the colors normally formed in the enamel and the dentin. With the uniform color system of the material from which laminate veneers have been composed, it is not possible to achieve an appearance significantly close to that of a natural tooth. It is therefore desirable to provide a laminate dental veneer having more nearly the characteristics, appearance and color of a normal human tooth.

DESCRIPTION OF THE PRIOR ART

Prior art patents related to the present invention include the following: U.S. Pat. No. 3,004,343 of Rydin relates to the manufacture of artificial teeth which incorporate a blank forming the labial or buccal surface, the blank being hand painted before attachment of its painted surface to the artificial tooth structure. U.S. Pat. No. 3,046,657 of Menter, et al., discloses a metal protective covering for bovine teeth which encompasses the entire tooth surface. The protective cover is formed to the tooth structure and is cemented in place. U.S. Pat. No. 3,327,016 of Lee, et al., discloses an epoxy bonding composition. U.S. Pat. No. 3,375,582 of Myerson discloses a prefabricated veneer for artificial dental teeth. U.S. Pat. No. 3,423,829 of Halpern, et al., discloses a bonding system for artificial teeth and resulting artificial tooth structure. U.S. Pat. No. 3,423,850 discloses a procelain and resin tooth with a silicon bonding agent. U.S. Pat. No. 3,483,618 discloses a dental crown construction and process of manufacture therefor. U.S. Pat. No. 3,647,498 of Dougherty teaches the provision of a dental filler composition from which artificial teeth and tooth repairs may be formed. U.S. Pat. No. 3,760,502 of Hirsh discloses precolored veneer structures which compose portions of dental crowns. West German Patent No. 2,008,781 discloses a dental crown structure incorporated a metal such as gold and a shell composed of acrylic and methacrylic acid polymerisate and mixture. Also of interest is a publication entitled "Laminate Veneer Restoration of Permanent Incisor Teeth" by Frank R. Faunce, D.D.S., and a publication entitled "the Use of Laminate Veneers for Restoration of Fractured or Discolored Teeth" by Frank R. Faunce, D.D.S., published in the Texas Dental Journal, August 1975.

SUMMARY OF THE INVENTION

It is therefore a primary feature of the present invention to provide a novel laminate dental veneer for attachment to a human tooth and which has the normal three-dimensional physical appearance and color of a normal human tooth.

It is also a feature of this invention to provide a novel laminate dental veneer, the outer surface of which is stain-resistant, chemical-resistant and is also resistant to erosion.

It is an even further feature of this invention to provide a novel laminate dental veneer which is composed tof layers, the outer layer being a dense, relatively hard material such as a cross-linked polymer, glass, procelain or the like, and a less dense or porous, or cellular inner layer or layers having the capability of efficient bonding to the labial surface of a tooth.

It is an even further feature of this invention to provide a novel laminate dental veneer incorporating an intrinsic color system including additive color centers and subtractive color centers which cooperate with the relative translucency of the veneer material to provide a three-dimensional, natural tooth-like appearance.

It is an even further feature of this invention to provide a novel composite laminate dental veneer embodying layered color centers which are dispersed in organized manner within the matrix of the veneer to provide enamel and dentin blends of color.

Among the several features of this invention is contemplated the provision of a novel electrostatic molding method of manufacturing laminate dental veneers according to the teachings of the present invention.

Briefly, the present invention relates to laminate dental veneers and particularly composite laminate dental veneers and the process for manufacturing the same wherein the veneers are provided with a color system having the three-dimensional shading and coloring characteristics of a normal tooth. The laminate veneer defines a stain-resistant, chemical-resistant and erosion-resistant outer surface which provides for long-wearing characteristics and promotes maintenance of natural tooth appearance and color throughout the service life thereof. In one form of the invention, the laminate dental veneers are of composite construction embodying an outer lamination composed of a suitable material that resists stains, chemical action and erosion. This outer lamination may be composed of a cross-linked polymer such as cross-linked polymethylmethacrylate or it may be composed of any one of a number of suitable vitreous materials such as ceramic material, glass and the like. The composite laminate dental veneer incorporates an inner lamination composed of a material having the capability of efficient bonding to the labial enamel or dentin surfaces of human teeth and also having the capability of permanent attachment to the outer lamination in such a manner as to define an integral veneer mass. This inner lamination may be composed of a non-cross-linked polymer such as noncross-linked polymethylmethacrylate which is fused to the outer lamination. The inner lamination with the outer lamination in attachment therewith is attached to the enamel labial surface of a tooth by means of any suitable luting compound. For example, an acceptable luting compound for bonding a noncross-linked polymethylmethacrylate lamination to the enamel tooth structure may be composed of diluted Bis-GMA compositie luting resin. If the laminations are composed of an outer layer of dense enamel-colored ceramic material and an inner layer of porous ceramic material, bonding may be achieved directly to the tooth surface by a suitable bonding agent without any need for the presence of a primer material on the layer of porous ceramic. In the case of a composite laminate dental veneer having an inner lamination composed of porcelain or glass, an inner layer of non-cross-linked polymethylmethacrylate or other suitable polymer may be fused to the inside surface thereof in order to provide for luting of the dental veneer to the enamel surface of the tooth by means of diluted Bis-GMA composite luting resin or other suitable luting agent.

The laminate veneer system of the present invention incorporates a color distribution system which functions together with translucent dental veneer materials to provide a three-dimensional appearance and color which closely approximates the appearance and color of a normal tooth. Color distribution is achieved by means of multi-layered, organized microdots of color which transmit, reflect and refract light in such manner as to give the veneer a three-dimensional characteristic when visualized. The color system incorporates an additive color center system and a subtractive color center system which function in cooperative manner to yield the desired three-dimensional color characteristics. In the case of multi-layered laminate veneers an additive color center system is employed in the outer lamination to provide enamel blends of white. An inner lamination of veneer material is provided with a subtractive color center system which provides dentin blends of color. Where cross-linked and noncross-linked polymers are incorporated within a laminated dental veneer an additive color center system is employed in the material of the cross-linked polymer layer while the inner non-cross-linked polymer layer incorporates the dentin blends of color of a subtractive color center system. These color center systems cooperate to provide a three-dimensional color characteristic including fluorescense, opalescence, enamel blends of white and dentin blends of color. In the event a bonding compound is employed for attachment of the veneer laminations into a single integral veneer mass, the bonding agent may also incorporate a color center system that functions in cooperative manner with that of the outer and inner layers to thus assist in the development of the desired three-dimensional color characteristics of a normal tooth and act as color toners. The outer lamination of a composite veneer is provided with blends of color including a cervical blend, and incisal blend and body blends of color which begin at the central portion of the body of the veneer and graduate or blend toward the respective cervical and incisal edges of the veneer. In the process of manufacture an initial veneer layer may be molded. Thereafter the subtractive color system may be introduced by painting cervical, incisal and body blends onto the veneer. A second or subsequent veneer layer or layers may then be molded to the initial layer which, under heat and pressure, fuses the layers into an integral veneer mass having the desired three-dimensional appearance and color characteristics.

In one suitable form of manufacture, an electrostatic molding process may be employed wherein polarized and charged microcrystalline prisms or particles are electrostatically sprayed or sputtered against oppositely charged and thus electrostatically attractive labial half of a tooth mold. These microcrystals will become aligned relative to one another thereby developing an organized layer of microcrystals which are electrostatically held against the charged half of the mold. These layered organized microcrystals are then sprayed with one or more layers of various resin materials, plastic or resin blends which microscopically flow around the aligned and polarized crystals forming a smooth surface against the labial surface of the mold and fixing the charged crystals in place. It is possible that layered resins and crystals of various configurations might be employed to achieve the proper reflection and refraction characteristics needed to enhance the color and color shaded characteristics of the resins.

In another form of manufacture the laminate dental veneers may be manufactured by means of a multi-step molding process wherein each of the laminations thereof is separately molded and, at the time of molding, is provided with its respective additive color center system or subtractive color center system. After this has been done the veneer laminations are then brought into integral assembly and are fused or bonded together to form an integral composite veneer having the desired color characteristics and also having characteristics for efficient luting to the enamel surface of the tooth.

BRIEF DESCRIPTION OF THE DRAWINGS

So that the manner in which the above recited features, advantages and objects of the invention, as well as others, which will become apparent, are attained and can be understood in detail, a more particular description of the invention, briefly summarized above, may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

In the Drawings

FIG. 1 is a labial view of a composite laminate veneer constructed in accordance with the present invention.

FIG. 2 is a horizontal cross-sectional view of the composite laminate veneer set forth in FIG. 1, the cross-section being taken along line 2—2 of FIG. 1.

FIG. 3 is a vertical cross-sectional view of the composite laminate veneer of FIG. 1, the cross-section being taken along line 3—3 of FIG. 1.

FIG. 4 is a labial view of a dental veneer constructed in accordance with this invention and being cross-hatched to illustrate areas of color shading showing the relationship of cervical, incisal and body color blends.

FIG. 5 is a cross-sectional view of the labial half of a mold enabling molded manufacture of composite dental veneers constructed in accordance with the present invention.

FIG. 6 is an enlarged fragmentary cross-sectional view of the mold of FIG. 1 showing layered organization of microcrystals accomplished by an electrostatic molding process together with layers of matrix material which form an integral laminate mass with the organized microcrystals.

FIG. 7 is a sectional view of both halves of the laminate veneer mold of FIG. 4.

DETAILED DESCRIPTION OF PREFERRED EMBODIMENTS

As mentioned above, this invention concerns the utilization of glass, silicons, silicates, or ceramic, or ceramic polymer composites, or glass polymer composites, or polymer composites that are filled or nonfilled, or polymers that are cross-linked or noncross-linked in the formation of dental laminate veneers. In one form, the laminate veneer dental laminate veneers. In one form, the laminate veneer consists of an outer layer or lamination of a dense, abrasion resistant and color stable glass or ceramic, ceramic polymer composite, glass polymer composite, polymer composite or a cross-linked polymer. The preferred cross-linked polymer is cross-linked polymethylmethacrylate. This outer layer of the laminate veneer contains color pigments of an enamel blend which utilizes elements of the color additive system. The outside surface of the outer lamination provides a high spectral reflectance. The inside lamination of the laminate veneer which is fused to the outside layer at the time of manufacturing, would be composed of a suitable porous glass or ceramic, ceramic polymer composite, a porous glass polymer composite, a porous polymer composite filled or nonfilled or a noncross-linked polymer such as polymethylmethacrylate. The materials that form the inner layers of the composite veneer should not be as dense as the outer layers and should be somewhat porous and cellular and unglazed or unfilled to permit efficient luting or bonding to the enamel tooth surface. The preferred noncross-linked polymer is noncross-linked polymethylmethacrylate.

The inner lamination contains transparent or translucent color pigments of a dentin blend which utilizes elements of the color subtractive color system. These color pigments are distributed in color centers or microdots of color that are layered in the translucent material to thus introduce a three-dimensional color effect.

The veneer configuration presently manufactured in accordance with U.S. Pat. No. 3,986,261 comprises a polymer resin laminate veneer in the form of a single layer with a uniform color system throughout its thickness. The present invention introduces a laminate veneer that is composed of other resins or glass or ceramic or glass ceramic composite resin materials or combinations thereof which are defined by multiple layers of material and color pigments. It make no difference whether the resin be a urethane based resin that is cross-linked or a Bis-GMA resin that is cross-linked or a cross-linked polymethylmethacrylate or any other diacrylate or polymer resin system or any glass or ceramic system or any combination of polymer, glass or ceramic. Many of these systems, whether they are filled or unfilled, could be used for the laminate veneer. It is essential that the outside layer of the laminate veneer be on the order of 1/10th to 5/10ths millimeters in thickness. If the veneer is composed of a polymer, then the polymer should be a dense cross-linked polymer resin. The polymer resin that is utilized in preference is a cross-linked polymethylmethacrylate for the outer lamination. In this outer lamination of the laminate veneer is provided all of the enamel blending color. The enamel blending color outer layer of the laminate veneer employs the color additive system. The basic colors that could be used are the yellows, blues, the greens, the magentas, the cyans and the red colors to pick up the enamel blends of white. The transmitted color systems and the reflective color systems in the inner layers are the color pigments that are translucent to the outer layer of the cross-linked resin. The thinner inside resin layer is on the order of 1/10th to 3/10ths millimeters thick. It could be composed of a porous glass or ceramic or a polymer or a glass or ceramic-polymer combination. It could also be composed of a noncross-linked polymer either of the urethane, Bis-GMA or of the polymethylmethacrylate or any other suitable polymer system that may use the color subtractive color system. This inner layer would be somewhat porous and fused to the outer layer of the laminate veneer. It is essential that the inner layer be thin and somewhat porous so that any combination of plastic material that is used for luting the laminate to the surface of the tooth has less material for the co-polymers or bonding primers to penetrate and more surface area for attachment. The noncross-linked polymer resin defining the inside surface of the veneer is molded and may be attached to the outer layer at the time of the processing of the laminate veneer. During the manufacturing process the veneer laminations are molded under heat and pressure or under vacuum and heat so that the ceramic or glass or ceramic glass polymer or composites or any other suitable substance cross-linked or noncross-linked polymer resins that make up the multiple layers are for all practical purposes fused together into an integral veneer mass. This specific molding process, however, is not in any way intended to limit the types and characteristics of the materials that may be utilized to form the composite veneers. It is only essential that the outer layer of the laminate veneer be dense and highly abrasion resistant and that the color system provide the three-dimensional color and shading characteristics of a normal tooth. The inside layer should be porous and capable of being bonded to the outer laminations of the veneer thus produced, and should be provided with the dentin shade colors which employ the color subtractive system. These colors could be magenta, yellow and cyan colors as the primary colors of the system for the dentinal shades of the inner laminations. These colors could come from the inside layer of the laminate and may contain opalescent and luminescent materials that would give the veneer a pearl-like quality. The color subtractive system could also have translucent and transparent color centers that would provide a three-dimensional effect for the laminate veneer so that in a very thin layer the veneer would have the effect of a fully color blend for a tooth. The polymer resin laminate veneer in its naturally molded configuration would be a laminate veneer that upon outward appearance would have the full coloring system of a natural tooth. The luting resin could then act to tone the laminate and change the color values either lighter or darker as the dentist may desire. The emphasized noncross-linked resin system, because of its noncross-linked nature, would chemically bond to the many current luting resin systems. For example, if a noncross-linked polymethylmethacrylate is employed, a primer system could be used employing methylene chloride or ethyl acetate plus a co-polymer of methylmethacrylate monomer or a polymethylmethacrylate. Either the methylene chloride or the ethyl acetate as the solvent could be used with the copolymer of either polymethylmethacrylate, methylmethacrylate or any other suitable resin material for luting. This primer softens the inside noncross-linked resin layer and prepares it so that when the Bis-GMA composite is employed, which may be diluted with methylmethacrylate monomer or any suitable diluent, or if a urethane resin system is employed, which may also be diluted, efficient bonding is established between the methylmethacrylate portion of the composite resin and the methylmethacrylate portion of a noncross-linked polymethylmethacrylate. Thus, a chemical bond is provided between the two layers and since the noncross-linked layer would be mechanically bonded, as well as chemically fused to the outer abrasion-resistant cross-linked resin or a ceramic or a glass or a combination polymer composite or glass, there is provided a laminate dental veneer in the truest sense of the word. Multiple layers of ceramic, glass and/or resin are placed in integal assembly to form a unitary veneer mass. The resin that is used to lute the laminate to the surface of a tooth presents the capability of penetrating into the micropores of the enamel caused by current etching techniques using a phosphoric acid, a citric acid or any of the acids that are commonly used presently to prepare the surface of the enamel to change it from a low energy to a high energy surface receptance state for bonding of the surface of the tooth and the laminate luting resin of the laminate veneer.

In essence, a cross-section of a laminate veneer restoration from the outer surface of the laminate veneer through the tooth would be of multiple character. The outer layer of the laminate veneer could be composed of a highly cross-linked polymethylmethacrylate, a ceramic or a glass or a ceramic-polymer composite or a glass-polymer composite or a polymer composite, filled or unfilled. This outer layer could be on the order of 1/10th to 5/10ths millimeters thick. The laminate veneer would comprise an inside layer of noncross-linked polymethylmethacrylate or a porous or cellular ceramic or glass or ceramic polymer composite or glass polymer composite or polymer composite, filled or unfilled, which would be porous and noncross-linked. The middle layers would be cellular and 1/10th millimeter or less in thickness. The inside laminate layer would be on the order of 1/10th to 2/10ths millimeters thick. In this manner a sandwiched laminated veneer is provided that would enable achievement of the full, three-dimensional color of a natural tooth in a very thin film. Clinically, when the laminate veneer is placed, the inside layer of the laminate veneer would be primed with a suitable primer and then would be bonded to a layer of a luting resin that would be approximately 1/10th to 2/10ths millimeters thick. This luting resin may comprise either a urethane based resin or a Bis-GMA based resin, or any other polymer resin system. This luting agent could then be attached to a thin layer of a sealant resin which could be a highly diluted Bis-GMA or an urethane based polymer that would be diluted with methylmethacrylate or propylene glycol dimethacrylate, or any other suitable diluent. In such manner, a system is provided whereby the laminate would be permanently bonded to the surface of the tooth and the color systems that are utilized provide the full three dimensional characteristics of a normal appearing tooth. The laminate veneers then have the reflectance and translucency of the outer layers, the reflecting, transmitting and refracting characteristics of the inside layers of a noncross-linked resin. The luting resin and a toner sealant are employed which have opaque or semi-transparent reflecting particles such as titanium dioxide or other color particles of a color additive or color subtractive system that would provide a reflective surface to cover any staining or any discoloration of a tooth surface. In this way, the light as it enters the outer layer of a cross-linked polymethyl methacrylate laminate or, for example, a ceramic laminate, if it is used, would be refracted because of its high density surface. Some light would be reflected because of the reflectance of the outside surface. The light would be transmitted and filtered and then bent at the interface between the noncross-linked and the cross-linked resins or the ceramic and the noncross-linked resin. Since the noncross-linked resin has a lower density, the light it would be refracted again and because of the dispersion of the color pigments or particles or color microdots or color centers that are transmissive or transparent in nature within the entire laminate, a filtering and scattering of light would occur. In the luting resin, which could be a urethane based composite or a Bis-GMA based composite, the veneer could also have opaque, semi-transparent, reflecting and opalescent and luminescent materials. As the light enters the noncross-linked inner polymethylmethacrylate layer, these resins would cause further reflection and scattering of light so that when the light reflects from the two surfaces, it would again be refracted and pick up the color from the back side of the translucent layer of the enamel layer, which may be either a ceramic, a glass, or cross-linked polymethylmethacrylate resin. The dental veneer employs the natural color selective system that the tooth utilizes to give a normal natural appearance to the laminate veneer, which provides a high luster and a translucency superior to currently used porcelain that has somewhat of a glassy effect, if not properly done. This would also eliminate the problem of metamerism which is now present in ceramic and polymer coloring systems for teeth. The color subtractive system basically is used in the inside noncross-linked layer of the laminate veneer. The color additive system would basically be used in the enamel blend of the outer lamination of cross-linked polymethylmethacrylate ceramic or glass or a composite of ceramic or glass or a polymer composite portion of the laminate veneer.

The configuration of the laminate veneer restoration on a tooth would be approximately 2/10ths to 7/10ths millimeters thick in the middle of a laminate at its thickest point. That thickness includes the thickness of the ceramic layer or the cross-linked layer as well as the noncross-linked layers that have been fused together. The thickness of the veneer remains constant except at the line angles at the periphery or proximal line angles of the margins where at the line angle curvature, the thickness would taper down to approximately 1/10th to 5/10ths millimeters thick. The laminate would then gradually taper toward the margins to a thickness of 2/10ths millimeters or less. The outside configuration of the laminate veneer would be a highly glazed lustrous reflective surface with the full anatomy of the normal natural tooth, and the inside surface would differ somewhat in appearance, having a frosted appearance because the inner surface would not be glazed and would be porous. Because of the nature of the ceramic, glass or the plastics that are used, the material will also be somewhat thermoplastic and be able to be molded by heat molding techniques that are set forth in my U.S. Pat. No. 3,986,261. The laminate veneer also has some degree of flexibility to enable the doctor to place the laminate more expertly and more precisely. The laminate also has a high resistance to breakage, chipping or abrasion. By having the color within the layers of the laminate veneer, the laminate would be color stable and nonfading, would eliminate metamerism, and would be highly resistant to stain. The highly glazed outer surface would give the normal spectral reflectance of a natural tooth. The bonding of the laminate to the tooth surface would be superior to the bonding of current laminate veneers.

Elements of the color additive color system, the subtractive color system and the partitive or additive spatial color fusion systems are evident in the perception of color blends in tooth enamel and dentin. Because the enamel is crystalline with minimal organic matrix, the crystals transmit, reflect and absorb light selectively. In a normal tooth, the crystalline prisms transmit and reflect light much as a cut diamond would. This transmission and reflection of light follows the color additive system for colored lights and thus the enamel appears to be white. The dentin, on the other hand, contains a great deal of organic material and less inorganic crystalline prisms and thus tends to absorb and reflect light. The reflected light gives an image of color since some of the light waves are selectively absorbed or filtered and allows colors basically in the yellow, orange and red range to be reflected back to the enamel which has a white or a blue-white color. The dentin then tends to follow the color subtractive systems such as is used in light filters that are commonly used in photography. The primary colors in additive or transmitted light (not pigments) are red, green and blue. Cyan, yellow and magenta are the additive secondary colors and are obtained by the mixing of two primary lights. When all three additive primary colored lights are combined, white light is the result. Additive color applies only to light. When any primary additive colored light is added to the secondary color directly opposite it, white light again results. This combination of a primary colored light and its opposing secondary colored light is known as "complementary colored light." Whenever two primary colored lights are mixed, the secondary color is brighter, and thus, when color centers or crystalline microdots are used in the laminate, a more brilliant and vital and lifelike appearance in a very thin laminate is possible.

On the other hand, the subtractive color system refers primarily to the dentin and is the basis for colored light filters. When light (full spectral light) is passed through a filter, some wavelengths are selectively absorbed and therefore subtracted from the spectral content of the light that entered the filter. The light that emerges (or reflected) from that filter is missing those particular wavelengths. This is the basis for the color subtractive system. The subtractive system is the converse of the additive system. The subtractive primary colors are cyan, magenta and yellow. The secondary colors of the subtractive filtered light system are red, blue and green. The secondary colored lights from the subtractive filter system are less bright. When all three subtractive primary colored lights are mixed or filtered, all light is absorbed and black results. The subtractive system and concepts refer to transparent pigments or filters such as the organic portion of the dentin. Therefore, the subtractive system refers more to the dentin which absorbs and reflects and is usually a yellowish color. The resin pigments or polymer pigments that are employed in the inner layer of the laminate veneer are also transparent and act as a filter, much as the organic material of the dentin does. Partitive color or "additive spatial fusion of color" is a psychological color system. The primary colors of this system are red, green, blue and yellow. Psychologically, there are four primary colors. The pure subtractive system applies to pigments that are transmissible and not opaque. When color pigments which are opaque, or semi-transparent such as are seen with the opaquing sealants with laminants, e.g. titanium dioxide suspended in diluted Bis GMA resin, then these opaquers or toners which do not meet all the pure tenets of either the additive or subtractive color theories, will react with some aspects of both systems. Such color behavior is known as partitive color or additive spatial color fusion. The additive result for mixing subtractive complementaries is an example of partitive color. The enamel blend portion of the laminate veneer, e.g. the outer ceramic, glass-ceramic or glass-polymer or dense cross-linked polymer, utilizes the color additive systems. The inner noncross-linked polymer layers, porous and cellular glass or ceramic layer or bonding layer which also contains the microdot or color centers of transparent color pigments which may be layered much as in photographic film color pigments, utilizes the color subtractive systems. The luting materials or opaque or toner sealant materials which contain opaquing or semi-transparent colored pigments that are used in bonding the laminate to the tooth follow the partitive or the additive spatial color fusion system. Thus, when all these systems are put together, the laminate veneer with its outer dense layer or layers with the color blend of the additive system and the inner layer or layers of dentin color of the subtractive system is bonded to the tooth by the luting agents and the sealants which contain elements of the partitive color system, then in a very thin layer or very thin film, the total restoration gives the appearance of a normal natural colored tooth without the corresponding thickness that is currently in effect with all other restorations used in dentistry, particularly porcelain crowns and does so without the effect of metamerism or color change when viewed under different light sources.

Referring now to the drawings and first to FIG. 1, a composite laminate dental veneer is illustrated generally at 10 which is in the form of an integral body 12 defining an upper cervical collar 14 and incisal edge 16 and opposed proximal edges 18 and 20. As illustrated particularly in FIGS. 2 and 3, the composite laminate veneer 10 incorporates an outer lamination 22 and an inner lamination 24 which are assembled in accordance with the foregoing teachings in such a manner as to define an integral laminate mass.

In FIG. 4 the composite laminate veneer structure of FIG. 1 is shown to employ a color system incorporated blends of color that assist in creating the three-dimensional appearance that is described above. The body portion 12 of the veneer defines an upper cervical body blend of color extending generally from the central portion of the veneer toward the cervical collar 14. This cervical blend of color extends to the cervical color which is provided with a cervical blend of color. The lower portion of the laminate veneer provides an incisal body blend of color which extends generally from the central portion of the tooth downwardly to the incisal edge. The incisal edge is provided with an incisal blend of color shown by the different color shading characteristics. The cervical body blend of color is identified by color area A while the cervical blend of color at the cervical collar of the laminate is identified by color area B. Color area C identifies the incisal body blend of color while color area D identifies the blend of color at the incisal edge of the tooth. By shading the laminate veneer in these particular areas, a three-dimensional appearance is effectively promoted. In the case of a composite laminate veneer composed of a polymethylmethacrylate polymer system, the ideal thickness in the central portion of the laminate veneer would be on the order of 5/10ths millimeters and the thickness at the line angle at the middle of the curvature would be on the order of 3/10ths millimeters. The thickness of the veneer composite at the margins would be on the order of 0.15 millimeters. The color would be overlapped in color areas A, B, C and D so that the color pigment centers would create a pointillistic effect in the viewer's mind. The color centers would be layered and spaced within the matrix of the polymer such that a three-dimensional color effect would be provided.

Referring now to FIGS. 5, 6 and 7 of the drawings, one suitable method of manufacturing composite laminate dental veneers in accordance with the present invention may conveniently take the form illustrated. As shown in FIG. 5, a labial mold plate 30 is shown to be formed in such manner as to define the labial surface configuration 32 of a laminate veneer to be manufactured. The labial surface plate 30 is provided with an electrostatic charge such as a positive charge for example. As shown in FIG. 6, which is a fragmentary sectional view representing a portion of the labial surface plate of FIG. 5, microcrystals are shown to be layered onto the labial surface of the mold. This is accomplished by providing microcrystals and charging them to an opposite polarity as compared with the polarity of the charged labial plate 30. As shown in FIG. 6, the initial layer at the labial surface of the laminate veneer is composed of microcrystals in the form of microprisms which are particularly oriented relative to one another.

The microprisms of the outer layer 34 are charged particles which become organized when placed in assembly with the oppositely charged mold plate 30. After the layer 34 of microcrystals has been implaced, a layer 36 of a securing matrix such as any one of a number of suitable polymer materials, is layered onto the microcrystals thus securing them in organized assembly. This matrix penetrates the interstices of the microcrystal layer 34 and thus cooperates with the microcrystals to form an integral mass therewith. If desired, a second layer 38 of microcrystals may be placed in assembly with the matrix 36. Here again, the microcrystals may be organized electrostatically by means of charges on the labial mold and microcrystals of opposite polarity. After implacement of the layer 38 of microcrystals, one or more layers of matrix such as shown at 40 and 42 may be brought into assembly with the microcrystal layer 38. If desired, the matrix material may conveniently take the form of a resin which is sprayed in layers for the purpose of fixing the aligned particles or microcrystals in proper position.

As shown in FIG. 7, a charged shader mold 44 may be brought into assembly with the labial surface mold 30 and a final layer of matrix material may be injected against the layered surface of the laminate to develop a veneer configuration and dimension of final form.

Polarized and charged microcrystalline prisms or particles are electrostatically sprayed or sputtered against an oppositely charged and thus electrostatically attractive labial half of a tooth mold. The electrostatic charge causes alignment of the microcrystals which will then be electrostatically held against the charged half of the mold. The microcrystal layer is then sprayed with layers of various resins, plastics or resin blends which microscopically flow around the aligned and polarized crystals forming a smooth surface against the labial surface of the mold and fixing the charged crystals in place. It is possible that layered resins and crystals of various configuration might be employed to achieve the proper reflection and refraction characteristics needed to enhance the color and shaded layers of resins.

The crystals and resins are sprayed in metered fashion and speed in order to achieve proper thickness and a uniform surface configuration. The nozzle size and rate of spraying could be controlled by means of a computer so that reproduceable results could be achieved in simple and efficient fashion. The surface resin could be of a relatively nonabradable nature and the subsequent resins selected to achieve proper color, translucency, reflection and refraction in order to produce an aesthetically pleasing laminate veneer and to make the laminate veneer easily moldable to the surface of a tooth. This feature permits the development of a laminate veneer configuration which is stress-resistant. It is envisioned that the flexible and moldable laminate veneer would then be rendered rigid by means of a commonly understood catalytic process provided on the surface of the tooth. After the computer-controlled and metered layers of crystals and resin are sprayed against the charged surface of the mold, the shader portion (lingual half) is closed against the labial plate and a final layer of resin is injected into the mold to produce the final form of the veneer. The plastic material and crystals are then fused or bonded into position under heat and pressure to produce a laminate veneer that is layered to reduce stress, improve aesthetics and provide a laminate veneer that can be intimately molded to a tooth and still retain its proper dental anatomy without deformation. If desired, the matrix providing structural support for the microcrystals may be composed of any one of a number of vitreous substances such as ceramic material, glass and the like.

A simple technique for manufacture of laminate veneers having desired three-dimensional appearance and natural color characteristics of a normal tooth may be accomplished with a double closure molding and coloring procedure. Enamel blends of fluorescent and opalescent agents may be employed in the exterior layer of the composite veneer. After first molding the outer layer of dense material such as cross-linked polymer with color additive centers, the mold is opened. The mold is opened after the outer layer has been formed. Color centers are then introduced such as by painting the inner surface of the formed outer layer with the subtractive color system. High intensity color pigments would be employed. The mold is then closed a second time and the second or inner lamination is molded to the outer layer. The substractive color system is thus encapsulated within the integral veneer mass that is formed. On the second closure of the mold a different shader mold half is typically employed to ensure efficient control of veneer thickness. In essence the veneer lamination is formed of material having fluorescent and opalescent in the outer layer (enamel portion). The inside layer is then formed and simultaneously fused to the outer layer. This causes fusion of the additive and subtractive color systems thus resulting in a very thin integral dental veneer having integrated additive and subtractive color systems which provide natural tooth color and the pearl-like three-dimensional appearance of a natural tooth.

In view of the foregoing, it is thus evident that I have provided a novel composite laminate veneer which effectively provides all of the objects and features hereinabove set forth together with other unique characteristics that are evident from the above detailed description. Although the invention has been described with regard to various specific embodiments thereof, these embodiments are not in any way intended to limit the scope of the invention. It is intended that the invention include other embodiments which fall within the scope of the claims set forth hereinbelow.

What is claimed is:

1. A composite laminate dental veneer for attachment to the etched labial enamel surfaces of a human tooth, comprising:
   (a) an outer lamination composed of stain-resistant, chemical-resistant and erosion-resistant cross-linked polymer material;
   (b) an inner lamination composed of a non cross-linked polymer material having the capability of efficient bonding to the etched labial enamel surfaces of human teeth and having the capability of permanent bonding to said outer lamination, said inner and outer laminations defining integral mass, said lamination defining incisal, cervical and marginal edges and conforming to the configuration of the labial surface of said human tooth;
   (c) said outer lamination being translucent and having additive color pigments; and
   (d) said inner lamination having subtractive color pigments.

2. A composite laminate veneer as recited in claim 1, wherein:
   (a) said additive color system comprises enamel blends of color pigments incorporated within said outer lamination; and
   (b) said subtractive color system comprises dentin blend of color pigments incorporated within said inner lamination.

3. A composite laminate veneer as recited in claim 1, wherein:
   said composite laminate veneer is heat deformable to the configuration of the tooth to which it is to be attached.

4. A composite laminate veneer as recited in claim 1, wherein:
   said inner and outer laminations are fused together to form said integral mass.

5. A composite laminate veneer as recited in claim 1, wherein:
   said inner and outer laminations are brought together in the presence of a bonding medium which secures said laminations in assembly to form said integral mass.

6. A composite laminate veneer as recited in claim 1, wherein:
   a bonding material secures said inner and outer laminations in assembly, said bonding material employing a color system providing said veneer with a natural tooth color and translucency in all visible light wavelengths.

7. A composite laminate veneer as recited in claim 1, wherein:
   said inner and outer laminations have greatest thickness at the central portions thereof and define marginal portions tapering to this edges at said incisal, cervical and proximal edges.

8. A composite laminate veneer as recited in claim 7, wherein said laminate veneer comprises a color system incorporating:
   (a) a cervical enamel blend of color at the cervical edge portion of said veneer;
   (b) an incisal enamel blend of color at the incisal edge portion of said laminate veneer;
   (c) a cervical enamel body blend of color extending from the central portion of said laminate veneer to said cervical edge portion thereof; and
   (d) an incisal enamel body blend of color extending from the central portion of said laminate veneer to said incisal edge portion thereof.

9. A composite laminate veneer as recited in claim 8, wherein:
   said additive color system defines said enamel blends of color of said cervical, incisal, cervical body and incisal body portions of said laminate veneer.

10. A composite laminate veneer as recited in claim 9, wherein;
    said color blends are overlapped in such manner as to provide said laminate veneer with a pointillistic effect when visualized.

11. A composite laminate veneer as recited in claim 10, wherein:
    (a) said color blends are defined by layered color centers incorporating organized microdots of color; and
    (b) at least said outer lamination is sufficiently translucent as to permit reflection of light from said color centers.

12. A composite laminate veneer for attachment to the labial surface of a human tooth, comprising:

(a) an outer body lamination of stain-resistant, chemical-resistant and abrasion-resistant material of a group including a cross-linked polymer, ceramic and ceramic-polymer composite conforming to the configuration of the labial surface of said tooth, said body defining a cervical edge portion, an incisal edge portion and proximal edge portions, said body being sufficiently translucent to permit transmission of light waves at least partially therethrough;

(b) layers of additive color pigments forming enamel blends of color and being situated in said outer body in such manner as to reflect light waves penetrating said body, said layers of color pigments providing said body with the appearance and color of a normal tooth in light of all visible wavelengths; and (c) an inner body lamination of a material from the group including ceramic, ceramic-polymer composite, porous polymer and cross-linked polymer, said inner lamination containing dentin blends of color pigments utilizing elements of the subtractive color system distributed in layered microdots of color.

13. A laminate veneer for attachment to the labial surface of a human tooth as recited in claim 12, wherein: said color pigments are sensitive to light of predetermined wavelength and change color responsive to being exposed to said predetermined light wavelengths to permit color adjustment before and after installation on said tooth.

14. A laminate veneer as recited in claim 12, wherein said body is formed by:

(a) an outer lamination of dense material for wear- and stain-resistance; and (b) said inner lamination being fused to said outer lamination and being composed of a less dense material for efficient bonding thereof to the enamel surface of a tooth.

15. A laminate veneer as recited in claim 14, wherein: said subtractive color pigments are located at the interface between said inner and outer body laminations and said additive color pigments are disposed in said outer lamination.

16. A laminate veneer as recited in claim 14, wherein said subtractive color pigments are applied to said outer lamination and said inner lamination is fused to said outer lamination causing said subtractive color pigments to be fused into the materials of said inner and outer laminations at the fusion interface therebetween.

* * * * *